US011179190B2

(12) United States Patent
Butler

(10) Patent No.: US 11,179,190 B2
(45) Date of Patent: Nov. 23, 2021

(54) LAPAROSCOPIC FORCEPS ASSEMBLY WITH AN OPERABLE MECHANISM

(71) Applicant: GYRUS ACMI, INC., Southborough, MA (US)

(72) Inventor: William Butler, Minneapolis, MN (US)

(73) Assignee: Gyrus Acmi, Inc., Westborough, MA (US)

(*) Notice: Subject to any disclaimer, the term of this patent is extended or adjusted under 35 U.S.C. 154(b) by 601 days.

(21) Appl. No.: 15/839,218

(22) Filed: Dec. 12, 2017

(65) Prior Publication Data

US 2019/0175256 A1    Jun. 13, 2019

(51) Int. Cl.
*A61B 18/14* (2006.01)
*A61B 17/29* (2006.01)
*A61B 18/00* (2006.01)

(52) U.S. Cl.
CPC ...... *A61B 18/1445* (2013.01); *A61B 17/2909* (2013.01); *A61B 2017/2912* (2013.01); (Continued)

(58) Field of Classification Search
CPC ........ A61B 2017/2919; A61B 18/1442; A61B 18/1445
See application file for complete search history.

(56) References Cited

U.S. PATENT DOCUMENTS 5,009,661 A    4/1991   Michelson
5,286,255 A    2/1994   Weber
(Continued)

FOREIGN PATENT DOCUMENTS

CN    106232038 A    12/2016
CN    106955129 A     7/2017
CN     19907796 A     6/2019

OTHER PUBLICATIONS

"Chinese Application Serial No. 201810067442.6, Voluntary Amendment filed Sep. 23, 2019", 13 pgs.
(Continued)

*Primary Examiner* — Michael F Peffley
*Assistant Examiner* — Bo Ouyang
(74) *Attorney, Agent, or Firm* — Schwegman Lundberg & Woessner, P.A.

(57) ABSTRACT

An electrosurgical device comprising: (a) a stylet including: (i) a first jaw; (ii) a second jaw that is movable relative to the first jaw from a first position where the first jaw and the second jaw are open to a second position where the first jaw and the second jaw move towards each other to grasp tissue therebetween; and (iii) one or more jaw support rods connected to the first jaw, the second jaw, or both; and (b) a housing connected to the stylet and the stylet extending from the housing, the housing including: (i) an operable mechanism including: (1) a fourth link; (2) a second link; (3) a first link being connected to the fourth link via a first pivot and being rotatable relative to the first pivot, and connected to the second link at a second pivot so that movement of the first link moves the second link relative to the fourth link; and (4) a third link being connected to the second link at a third pivot so that movement of the second link moves the third link, and the fourth link being connected to the third link at a fourth pivot, the third link moving about the fourth pivot to move the one or more jaw supports so that the first jaw and the second jaw are moved between the first position and the second position; and wherein the fourth link is the housing and the first link is a clamp lever that extends outside of the housing and is actuated by a user.

19 Claims, 7 Drawing Sheets

(52) U.S. Cl.
CPC ............... *A61B 2018/00607* (2013.01); *A61B 2018/1452* (2013.01)

(56) References Cited

U.S. PATENT DOCUMENTS

| | | | |
|---|---|---|---|
| 5,354,313 A | 10/1994 | Boebel | |
| 5,413,583 A | 5/1995 | Wohlers | |
| 5,445,638 A | 8/1995 | Rydell et al. | |
| 5,480,409 A | 1/1996 | Riza | |
| 5,562,699 A | 10/1996 | Heimberger et al. | |
| 5,653,721 A | 8/1997 | Knodel et al. | |
| 5,683,412 A | 11/1997 | Scarfone | |
| 5,735,849 A | 4/1998 | Baden et al. | |
| 5,776,130 A | 7/1998 | Buysse et al. | |
| 5,944,723 A | 8/1999 | Colleran et al. | |
| 5,947,984 A | 9/1999 | Whipple | |
| 6,039,733 A | 3/2000 | Buysse et al. | |
| 6,113,596 A | 9/2000 | Hooven et al. | |
| 6,190,386 B1 | 2/2001 | Rydell | |
| 6,270,497 B1 | 8/2001 | Sekino et al. | |
| 6,458,130 B1 | 10/2002 | Frazier et al. | |
| 6,585,735 B1 | 7/2003 | Frazier et al. | |
| 6,679,882 B1 | 1/2004 | Kornerup | |
| 6,752,823 B2 | 6/2004 | Prestel | |
| 7,083,618 B2 | 8/2006 | Couture et al. | |
| 7,101,372 B2 | 9/2006 | Dycus et al. | |
| 7,118,587 B2 | 10/2006 | Dycus et al. | |
| 7,131,971 B2 | 11/2006 | Dycus et al. | |
| 7,384,420 B2 | 6/2008 | Dycus et al. | |
| 7,481,810 B2 | 1/2009 | Dumbauld et al. | |
| 7,604,634 B2 | 10/2009 | Hooven | |
| 7,628,791 B2 | 12/2009 | Garrison et al. | |
| 7,766,910 B2 | 8/2010 | Hixson et al. | |
| 8,298,232 B2 | 10/2012 | Unger | |
| 8,475,453 B2 | 7/2013 | Marczyk et al. | |
| 8,632,539 B2 | 1/2014 | Twomey et al. | |
| 8,647,341 B2 | 2/2014 | Dycus et al. | |
| 8,672,935 B2 | 3/2014 | Okada et al. | |
| 8,702,749 B2* | 4/2014 | Twomey | A61B 18/1445 606/205 |
| 8,734,443 B2 | 5/2014 | Hixson et al. | |
| 9,113,903 B2 | 8/2015 | Unger | |
| 9,113,940 B2 | 8/2015 | Twomey | |
| 9,579,117 B2 | 2/2017 | Kappus et al. | |
| 9,592,089 B2 | 3/2017 | Lyons et al. | |
| 9,681,883 B2 | 6/2017 | Windgassen et al. | |
| 9,839,471 B2 | 12/2017 | O'neill et al. | |
| 9,867,658 B2 | 1/2018 | Larson et al. | |
| 10,349,963 B2 | 7/2019 | Fiksen et al. | |
| 2006/0084973 A1 | 4/2006 | Hushka | |
| 2006/0235438 A1 | 10/2006 | Huitema et al. | |
| 2009/0112206 A1 | 4/2009 | Dumbauld et al. | |
| 2012/0241505 A1* | 9/2012 | Alexander, III | A61B 17/0643 227/179.1 |
| 2013/0131666 A1 | 5/2013 | Atwell et al. | |
| 2014/0135763 A1 | 5/2014 | Kappus et al. | |
| 2014/0135805 A1 | 5/2014 | Windgassen et al. | |
| 2017/0196624 A1 | 7/2017 | Nagtegaal et al. | |
| 2017/0196625 A1 | 7/2017 | Nagtegaal | |
| 2017/0354456 A1 | 12/2017 | Fiksen et al. | |
| 2018/0296213 A1* | 10/2018 | Strobl | A61B 18/1442 |
| 2020/0305960 A1 | 10/2020 | Butler et al. | |

OTHER PUBLICATIONS

"Chinese Application Serial No. 201810067442.6, Office Action dated Jan. 28, 2021", w/English Translation, 17 pgs.

"Chinese Application Serial No. 201810067442.6, Response filed May 21, 2021 to Office Action dated Jan. 28, 2021", with machine translation and English claims, 27 pgs.

* cited by examiner

LAPAROSCOPIC FORCEPS ASSEMBLY WITH AN OPERABLE MECHANISM

FIELD

The disclosure relates to forceps with a first working arm that is movable relative to a second working arm and specifically an operable mechanism that moves the first working arm relative to the second working arm.

BACKGROUND

Generally forceps may be utilized for laparoscopic surgery. The forceps may be used to control delicate movements inside a patient. These forceps may be used to grip an anatomical feature. The forceps may include a gripping assembly or a cutting assembly. The forceps may include electrical energy for use in the gripping assembly. The forceps have a pair of opposed resilient jaws that are closed against each other by pulling the jaws into a distal end of a shaft that captures a portion of the jaws that is wider than the distal end opening of the shaft so that the jaws are moved together. Similarly, the shaft may be pushed over the jaws so that the jaws are moved together to create a gripping force. In both of these the shaft captures the jaws and acts as a cam that forces the jaws together to create the gripping force. Examples of some forceps with resilient jaws closed by a camming action may be found in U.S. Pat. Nos. 5,445,638; 6,190,386; 6,113,596; 6,679,882, 7,118,587, and 8,734,443; and HALO cutting forceps, available at http://www.olympus-osta.com/halo.htm last accessed on Apr. 3, 2014 all of which are incorporated by reference herein in their entirety for all purposes.

It would be attractive for the forceps to include a device that controls an amount of force required to move the working arms. What is needed is a device that assists in beginning movement of a trigger that moves one or more working arms. What is needed is a device that assists in creating a gripping force that grips a feature of interest between two working arms. It would be attractive to have a device that has a low initial input force to begin to move the first working arm and the second working arm. What is needed is an operable mechanism that that has let off once clamping, cutting, or both reach a predetermined position or predetermined force is achieved so that an amount of force required to complete a cut, clamp, or both is reduced.

SUMMARY

The disclosure meets one or more of the needs by providing: an electrosurgical device comprising: (a) a stylet including: (i) a first jaw; (ii) a second jaw that is movable relative to the first jaw from a first position where the first jaw and the second jaw are open to a second position where the first jaw and the second jaw move towards each other to grasp tissue therebetween; and (iii) one or more jaw support rods connected to the first jaw, the second jaw, or both; and (b) a housing connected to the stylet and the stylet extending from the housing, the housing including: (i) an operable mechanism including: (1) a fourth link; (2) a second link; (3) a first link being connected to the fourth link via a first pivot and being rotatable relative to the first pivot, and connected to the second link at a second pivot so that movement of the first link moves the second link relative to the fourth link; and (4) a third link being connected to the second link at a third pivot so that movement of the second link moves the third link, and the fourth link being connected to the third link at a fourth pivot, the third link moving about the fourth pivot to move the one or more jaw supports so that the first jaw and the second jaw are moved between the first position and the second position; and wherein the fourth link is the housing and the first link is a clamp trigger that extends outside of the housing and is actuated by a user.

The teachings herein provide forceps that include a device that controls an amount of force required to move the working arms. The present teachings provide a device that assists in beginning movement of a trigger that moves one or more working arms. The present teachings provide a device that assists in creating a gripping force that grips a feature of interest between two working arms. The present teachings provide a device that has a low initial input force to begin to move the first working arm and the second working arm. The teachings provide an operable mechanism that that has let off once clamping, cutting, or both reach a predetermined position or predetermined force is achieved so that an amount of force required to complete a cut, clamp, or both is reduced.

DETAILED DESCRIPTION

Figure 1:
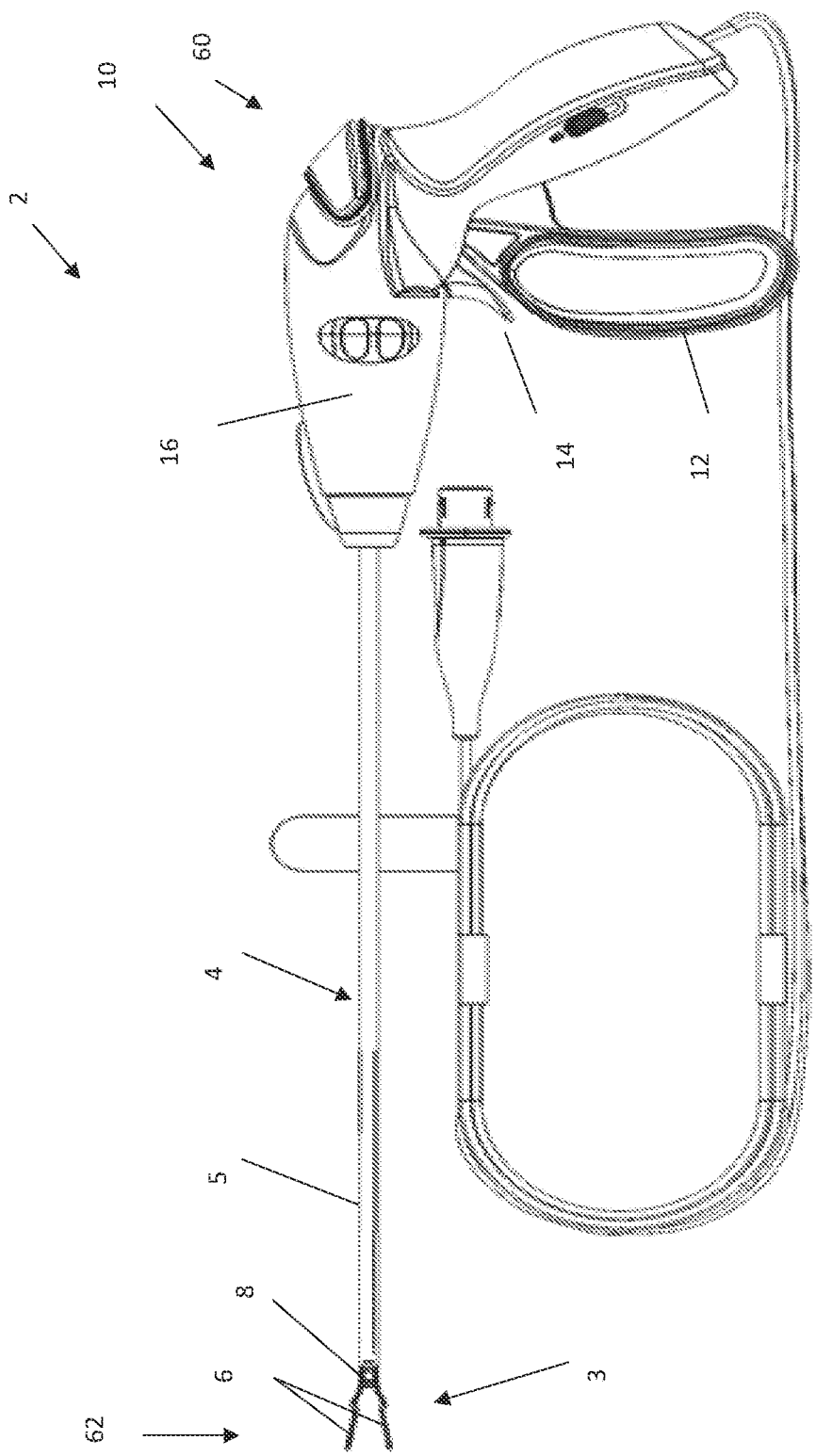
FIG. 1 illustrates a side view of laparoscopic forceps.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings relate to a surgical device. The surgical device may be a non-electrical device (i.e., may only provide mechanical functions). Preferably, the surgical device is an electrosurgical device. The electrosurgical device may provide one or more therapy currents. Preferably, the electrosurgical device provides two or more therapy currents (e.g., monopolar power and bipolar power). A therapy current may pass between the jaws (e.g., bipolar power). A therapy current may pass from a jaw to a blade or vice versa. A therapy current (e.g., monopolar power) may pass from a blade to a remote electrode (e.g., ground pad). The electrosurgical device may apply power before, after, or simultaneously with a mechanical technique (e.g., gripping or cutting). The electrosurgical device may include a distal end and a proximal end. The distal end may include a portion of a forceps device (e.g., jaws, blade, or both). The proximal end may be a portion a user grips (e.g., hand piece or housing).

The hand piece may function to form an enclosing structure for the forceps, a gripping portion for the user, a main portion for manipulating the forceps, a four bar mechanism, or a combination thereof. The hand piece may be any device that houses all or a portion of the working assemblies and parts of the forceps. The hand piece may be comprised of one or more housing structures. Preferably, the hand piece is two or more housing structures. The hand piece may be any structure that is gripped by a user. The hand piece may be any structure that combines one or more of the components discussed herein so that the surgical device is formed. The hand piece may assist in performing laparoscopic surgery. The hand piece may be ergonomically shaped. The ergonomic shape of the hand piece may be any shape so that the forceps may be used ambidextrously. The ergonomic shape of the hand piece may be any shape such that all the controls can be accessed by a single hand gripping the hand piece. The hand piece may be comprised of housing structures. The housing structures may be one or more devices that form the hand piece. The housing structures may be any devices that may affix certain pieces into position. The housing structures may form a cavity to house working assemblies of the forceps. The housing structures may be one or more housing structures and preferably two or more housing structures. The housing structures may be any device that includes a recess for receiving one or more components of the forceps. The housing structures may house one or more operable mechanisms. The housing structure may house all or a portion of a first link, second link, or third link of the operable mechanism. A user may grip the housing and operate one or more operable mechanisms (e.g., levers, links, or four bar mechanisms) to move the forceps, the blade, or both.

The one or more operable mechanism may function to move one or more jaws, both jaws, a blade, or a combination thereof. The one or more operable mechanism may include a four bar mechanism, a five bar mechanism, or even a six bar mechanism. The operable mechanism may include one or more rods (e.g., a blade support rod, a jaw support rod, or both). The one or more operable mechanisms may be or include one or more levers, links, triggers, or a combination thereof. If more than one operable mechanisms are present the operable mechanisms may include one or more common links. For example, each of the operable mechanisms may have a common fourth link. The one or more links may be a cut lever or cut trigger (e.g., that moves a blade), a clamp lever or cut trigger (e.g., that moves the jaws between an release position and a retract position), or both. The one or more levers may be an input that a user actuates to activate the operable mechanism. The one or more levers may be part of the operable mechanism. One lever or trigger may be part of the operable mechanism and one lever or trigger may be separate from the operable mechanism. The one or more operable mechanisms may be any device that may be manipulated or moved by applying pressure or a force to a portion of the one or more operable mechanisms with a hand, finger, foot, or a combination thereof to produce an output movement on an output element or apply an output force on an output element. The one or more operable mechanisms may be any device that may connect other moveable components, for example the tubular member, a cutting assembly, a blade assembly, a functional assembly, a jaw, a jaw support rod, or a combination thereof. The one or more operable mechanisms may be actuated ambidextrously. The one or more operable mechanisms may be a single operable mechanism that may be linked to two different functions and may be moved to generate each function simultaneously. For example, the operable mechanism may close two jaws together and move a blade between the two jaws. Preferably, the one or more operable mechanisms may be two operable mechanisms and each operable mechanism may be actuated to perform a different function. For example, there may be two levers or triggers and each lever or trigger may actuate one portion of the device. The two operable mechanisms may be a clamp operable mechanism and a cut trigger operable mechanism. An operable mechanism (e.g., four bar mechanism) may be connected to a clamp lever or clamp trigger and a separate four bar mechanism may be connected to a cut lever or cut trigger.

An operable mechanism may function to convert rotational movement into longitudinal movement. An operable mechanism may function to axially move one or more jaws, one or tubes (e.g., hollow tubes or solid tubes), one or more blades, or a combination thereof. The operable mechanism may include one or more tubes, support rods, or both. Each axially or rotationally moving member may be connected to an operable mechanism. Each operable mechanism may reduce an amount of force or torque needed to move one of the links (e.g., cut lever/cut trigger or clamp lever/clamp trigger) to move one or more jaws, one or more blades or both. A preferred operable mechanism is a four bar mechanism. The operable mechanism may have three or more force characteristics (e.g., torque if rotational movement or force if linear movement) or phases.

The force characteristics may have a first phase. The first phase may be a zero phase. In the first phase a constant force may be required to move the four bar mechanism. The first phase may continue from a release position to a contact position. For example, the first phase may begin with the jaws being open and continue until the jaws contact one another, a blade, tissue, a blade contacts tissue, or a combination thereof. The first phase may move the device with a torque of about 0.01 N-m or more, about 0.03 N-m or more, or about 0.05 0.04 N-m or more. The first phase may move the device with a torque of about 1.0 N-m or less, about 0.5 N-m or less, about 0.1 N-m or less, or about 0.05 N or less. The first phase may move the device with a force of about 0.2 N or more about 0.5 N or more, about 0.75 N or more, or about 1.0 N or more applied at a point approximately 2 inches from the pivot. The first phase may move the device with a force of about 5 N or less, about 3 N or less, about 2 N or less, or about 1.1 N or less applied at a point approximately 2 inches from the pivot. The first phase may end when an amount of force or torque required increases. Once the first phase is complete a second phase may begin and an amount of force required to move the four bar mechanism may gradually increase.

The second phase may function to begin cutting tissue, begin clamping tissue, or both. The second phase may fully clamp tissue, fully cut tissue, or both. Preferably, the second phase will begin clamping tissue, cutting tissue, or both and may continue until the tissue is partially cut or partially clamped. The second phase may be a partial pull position. The second phase may continue until about 20 percent or more, about 30 percent or more, about 40 percent or more, or about 50 percent or more of the tissue is cut, compressed by clamping (i.e., a thickness of the tissue is reduced by X percent of the total clamping compression)), or both. The second phase may continue from about 100 percent or less, about 90 percent or less, about 80 percent or less, or about 70 percent or less of the tissue is cut, compressed by clamping, or both. The second phase may have a positive slope. The second phase may have a linear slope. The second phase may have a slope that becomes smaller as the slope second phase approaches the third phase. The slope of the second phase may gradually decrease as the second phase approaches a peak where the second phase changes to a third phase. The second phase may end when an over-force protection mechanism has reached its trip point, the jaws are fully compressed, the feature of interest is fully compressed, an angle between a first link and a second link, an angle between a second link and a third link, an angle between a third link and a fourth link, or a combination thereof are achieved. The second phase may move the device with a torque of about 0.1 N-m or more, about 0.3 N-m or more, or about 0.4 N-m or more. The second phase may move the device with a torque of about 5.0 N-m or less, about 3 N-m or less, about 2 N-m or less, or about 1.7 N-m or less. The second phase may move the device with a force of about 5 N or more about 7 N or more, about 10 N or more, or about 12 N or more applied at a point approximately 2 inches from the pivot. The second phase may move the device with a force of about 50 N or less, about 40 N or less, about 35 N or less, or about 33 N or less applied at a point approximately 2 inches from the pivot. The amount of torque to move the device may gradually increase as during movement of the first link. For example, the amount of torque may increase from about 1.0 N-m to about 1.7 N-m as the second phase increases from the first phase to the third phase. Thus, a maximum torque applied may be about 1.7 N-m. The second phase may continue until an over-force protection mechanism has reached its trip point, the jaws are fully compressed, the feature of interest is fully compressed, an angle between a first link and a second link, an angle between a second link and a third link, an angle between a third link and a fourth link, or a combination thereof are achieved and then a third phase may begin.

The third phase may function to complete a cut, complete a stroke of a link, maintain a clamping load, complete a clamp, or a combination thereof. The third phase may be a "let off" when compared to a second phase. The third phase may be a plateau of torque or force to move the device or a link of the device. The third phase may have a slope of 0. The third phase may decrease an amount of force or torque needed to move the forceps, move the blade, or both. The third phase may have a negative slope. The third phase may have a linear slope. The third phase may have a slope that varies as the third phase moves away from the second phase. The third phase may be from a partial clamp to a complete clamp. The third phase may be from a partial cut to a full cut. The third phase may begin when the amount of force required to move the four bar mechanism reaches a peak and decreases or plateaus. The third phase may end when a complete stroke of lever is completed. The third phase may end when a maximum jaw clamp force or torque is met or a maximum blade advancement position is met. The third phase may move the device with a torque of about 0.1 N-m or more, about 0.3 N-m or more, or about 0.4 N-m or more. The third phase may move the device with a torque of about 4.0 N-m or less, about 3.0 N-m or less, about 2.0 N-m or less, or about 1.5 N-m or less. The third phase may move the device with a force of about 5 N or more about 7 N or more, about 10 N or more, or about 12 N or more applied at a point approximately 2 inches from the pivot. The third phase may move the device with a force of about 45 N or less, about 40 N or less, about 35 N or less, or about 30 N or less applied at a point approximately 2 inches from the pivot.

The one or more triggers function to be an input to an operable mechanism. The one or more triggers as discussed herein may be a lever, handle, link, or a combination thereof. The one or more triggers may be a cut trigger, a clamp trigger, or both that when actuated input movement into the operable mechanism so that the operable mechanism provides an output. If the triggers are a lever, the lever is a rigid member that turns on a pivot. The cut lever or cut trigger, the clamp lever or clamp trigger, or both may be a first link of an operable mechanism or a respective four bar mechanism. The cut lever, the clamp lever, or both may be a first link. The first link may function to move one or more jaws, one or more blades, a jaw support rod, a blade support rod, a second link, or a combination thereof. The first link may extend between a release position (e.g., a start position) and a retract position (e.g., a full pull position where the jaws are closed, a partial pull position, the blade is extended, or a combination thereof). The first link may have two legs.

The two legs of the first link may be a connection leg and an application leg. The first link may be generally "L" shaped. The connection leg may include one or more pivots, two or more pivots, one or more joint elements that connect to a pivot, two or more joint elements that connect to pivots, or a combination thereof. The connection leg may connect to the first link, the fourth link, or both. The one or more connection legs may be located partially within a housing or entirely within a housing. The connection legs may connect the first link to a second link and a fourth link. The one or more connection legs may be connected to an application leg and the application leg may connect to the connection leg and extend out of the housing.

The one or more application legs may be free of a pivot or a joint element (i.e., a location where a pivot connects to a link). The one or more application legs may be contacted by a user. The one or more application legs may move upon an application of force, an application or torque, or both. The one or more connection legs may be located partially inside or completely inside of a housing. The one or more application legs may extend out of the housing. The one or more application legs may have a portion that extends out of the housing and the user contacts the application leg to move the first link so that a connection leg portion of the first link provides an input. The one or more connection legs, application legs, or both may be located entirely outside of the housing or partially outside of the housing.

The first link may move relative to a second link, a fourth link, or both. The first link may be connected to both a second link and a fourth link. The first link may be a rocker link, a coupler link, or a ground link. Preferably, the first link is a rocker link. The first link may be free of a connection with a fourth link, a second link, a third link, or a combination thereof. The first link may be rotated around a pivot. Movement of the first link proximally (towards a retract position) may close the jaws, extend a blade or both. Movement of the first link distally (towards a release position) may open the jaws, retract a blade, or both. The first link may have a joint element connected at a first pivot and a joint element connected at by a second pivot. The links may extend between two joint elements. The joint elements may receive a pin or a connection device that allows two links to move relative to each other. A portion of a trigger, lever, or both may extend beyond a joint element of a link. The first link may be the longest link (e.g., longer than the second link, the third link, the fourth link, or a combination thereof). The first link in a start position may be positioned relative to one or more reference lines. The one or more reference lines may be a vertical reference line a horizontal reference line, or both. Preferably, the one or more first links have an angle or position that varies relative to a horizontal reference line. The horizontal reference line is a line that extends through the first pivot and parallel to the tube, the stylet, or both. An angle may be located between a horizontal reference line and a line that extends between the first pivot and the second pivot, and the angle may be sufficiently small in a starting position so that when the first link is moved, the jaws, blade, or both are moved. The angle in the starting position, the partial pull position, or a combination thereof may be about 5 degrees or more, about 10 degrees or more, about 15 degrees or more, or about 20 degrees or more. The angle in the starting position, the partial pull position, the full pull position, or a combination thereof may be about 90 degrees or less, about 60 degrees or less, about 50 degrees or less, or about 35 degrees or less (e.g., in the start position the angle is about 50 degrees, in the partial pull position the angle is about 22 degrees, and in the full pull position the angle is about 18 degrees). The first pivot and the second pivot of the first link may be located proximate or adjacent to each other.

The first pivot may connect the first link to a fourth link. The first pivot may connect to two joint elements (e.g., a joint element in a first link and a joint element in a fourth link). The first pivot may ground the first link. The first pivot may be a pin that the first link rotates around. The first pivot may extend from a fourth link to the first link so that the first link is movable relative to the fourth link. The pivots (e.g., first, second, third, fourth) may be cylindrical, a bearing surface, plastic, metal, a coated metal, a coated plastic, or a combination thereof. The pivots may be a bearing or have a low friction coating (e.g., polytetrafluoroethylene). The first pivot may be located proximate to a second pivot.

The second pivot functions to allow the first link and the second link to move relative to each other. The second pivot may connect a first link to a second link. The second pivot may connect to two joint elements (e.g., a joint element in a first link and a joint element in a second link). The second pivot may permit the second link to move relative to the first link so that a position of the second link moves in a distal direction or a proximal direction (e.g., has a portion that moves longitudinally) relative to the stylet, the fourth link, or both. The second pivot may permit the second link to change angles relative to the first link. The second link and the first link thereby have an angle that extends therebetween. The angles between the adjacent links may vary as the operable mechanism is moved from a starting position to a partial pull position or a full pull position. The angle may have a first side that extends through the first pivot in the first link along a longitudinal axis of the first link and a second side that extends through the second pivot of the second link along a longitudinal axis of the second link. The angle may vary as the first link is moved between a start position (e.g., release position), partial pull position, and a full pull position (e.g., a retract position). The angle between the first link and the second link may be between about 0 degrees and 180 degrees and preferably between about 90 degrees and about 175 degrees. The angle may be about 45 degrees or more, about 60 degrees or more, about 75 degrees or more, about 5 degrees or more, or about 90 degrees or more (e.g., about 103 degrees in a start position, about 158 degrees in a locked position, and about 165 degrees in a full pull position) when the first link is in the start position, locked position, or full pull position. The angle may be about 180 degrees or less, about 170 degrees or less, or about 165 degrees or less when the first link is in the start position, locked position, or full pull position. The angle change by about 15 degrees or more, about 25 degrees or more, about 35 degrees or more, or about 40 degrees or more when the first link is moved between the start position and partial pull position, the start position and the full pull position, or the partial pull position and the full pull position. The second pivot may be connected to a joint element of a first link and a joint element of a second link.

The second link functions to transmit a force, torque, or both from a first link to a third link. The second link permits the first link to move an end of a third link a distance further than the first link can move without the second link. The second link may pull an end of a third link or push an end of a third link. The second link may be partially located within the housing. Preferably, the second link is entirely located within the housing. The second link may be the shortest of the links (i.e., shorter than the first link, third link, fourth link, or a combination thereof). The second link may be a rocker link, a coupler link, or a ground link. Preferably, the second link is a coupler link. The second link may be pushed when the first link is moved from a release position to a retract position. The second link may be pulled when the first link is moved from an release position to a retract position. The second link may be connected to a third link at a third pivot.

The third pivot may function to allow the third link to move relative to the second link. The third pivot may connect to two joint elements (e.g., a joint element in a second link and a joint element in a third link). The third pivot rotationally moves one end of the third pivot relative to the second pivot so that an angle between the second link and the third link changes. The third pivot may move an end of the third link substantially along a longitudinal axis (e.g., the motion may be arcute or have a small curve but be relatively parallel to a longitudinal axis) of the stylet, the fourth link, or both. The third pivot may be located in an end or end region of a third link, a second, link, or both. The third pivot may be located entirely within a housing. The third link may permit an angle between the second link and the third link to change as the device is moved between a release position and a retract position. The second link and the third link may have an angle that extends therebetween. The angle may have a first side that extends through the second pivot in the second link along a longitudinal axis of the second link and a second side that extends through the third pivot in the third link along a longitudinal axis of the third link. The angle may vary as the first link is moved between a start position, a partial pull position, and a full pull position. The angle between the second link and the third link may stay within a range of about 90 degrees and about 45 degrees. The angle may be about 30 degrees or more, about 45 degrees or more, about 60 degrees or more, about 75 degrees, about 80 degrees or more, or even about 85 degrees or more (e.g., about 67 degrees in the start position, about 85 degrees in the partial pull position, and about 88 degrees in the full pull position) when the first link is in the start position, partial pull position, or full pull position. The angle may be about 130 degrees or less, about 110 degrees or less, about 100 degrees or less, or preferably 90 degrees or less when the first link is in the start position, partial pull position, or full pull position. The angle may vary by about 15 degrees or more, about 25 degrees or more, about 35 degrees or more, or about 40 degrees or more (e.g., about 45 degrees) when the first link moved between the start position and partial pull position, the start position and the full pull position, or the partial pull position and the full pull position.

The third link may function to move one or more jaws, one or more blades, or both. The third link may move one or more jaw support rods, a stylet, a tube, a solid tube, a blade, a blade support rod, or a combination thereof. The third link may move a tube relative to a jaw support rod, a blade support rod, or both. The third link may move a jaw support rod, a blade support rod, or both relative to a tube. The third link may be connected to a fifth link. The fifth link may be a jw support rod, a blade support rod, or both. The third link may be connected to a second link and a fourth link. The third link may be a rocker link, a coupler link, or a ground link. Preferably, the third link is a rocker link. The third link may have pivots at opposing ends. The third link may move in a generally linear manner. The third link may move in an arcuate manner. For example, the third link may be fixed laterally and longitudinally by the fourth pivot but can rotationally move about the fourth pivot such that the third end may move in a generally circular fashion with an arcuate movement. The movement of the third link may be sufficiently short so that the movement is generally linear (i.e., a change in elevation from a peak to a trough may be about 5 mm or less, about 3 mm or less, or about 1 mm or less along the movement of the third link). An end of the third link connected to the second link may move a distance that about ½ or less, about ⅜ or less, about ¼ or less a length of the second link. Although the third link may move in an arcuate manner the third link may move a longitudinal distance of about 5 mm or more, about 7 mm or more, about 1 cm or more, about 2 cm or more, or about 3 cm or more, or about 5 cm or more. The third link may move a sufficient distance to create a clamping force, cut tissue, hold tissue, move one jaw into contact with another jaw, or a combination thereof. The third link may be entirely located within the housing. The third link may have a portion that extends out of the housing. The third link may move along a follower surface of a stylet, tube, jaw support rods, blade support rod, or a combination thereof. An angle of the third link may vary relative to a reference line (e.g., a vertical reference line) as the third link moves from a start position to a full pull position, from a start position to a partial pull position, from a partial pull position to a full pull position, or a combination thereof. The reference line may be a vertical reference line. The vertical reference line may be perpendicular to a horizontal reference line, the stylet, a tube, or a combination thereof. The angle between the reference line and the third link may be about ±1 degree or more, ±2 degrees or more, ±3 degrees or more, or even about ±4 degrees or more in the start position, partial pull position, full pull position, or a combination thereof. The third link may be located on a first side (e.g., a positive side) of the vertical reference line when the third link is in a start position and on a second side (e.g., negative side) of the vertical reference line when the third link is in a partial pull position, full pull position, or both. Thus, for example, the angle of the third link relative to the vertical reference line may be about 4.2 degrees in the start position, about −3.9 degrees in the partial pull position, and about −4.3 degrees in the full pull position. An angle between the reference line and the third link may be about ±20 degrees or less, about ±15 degrees or less, about ±10 degrees or less, or about ±5 degrees or less. The third link may extend across the vertical reference line as the third link moves between a start position and a partial pull position or a full pull position. The third link may be in contact with or move a follower surface. The third link may include one or more cam surfaces that move along a follower surface or contact a follower surface to move one or more jaws, one or more blades, or both.

The follower surface may function to guide one or more links and preferably a third link in a longitudinal direction and preferably along a stylet. The follower surface may connect a third link to a fifth link. The follower surface may be an end of a fifth link. The follower surface may translate an input to a fifth link (e.g., a tube, a jaw support rod, a blade support rod, or a combination thereof) so that the fifth link provides an output. The follower surface may be a surface that functions to move or guide a jaw support rod, a blade support rod, a tube, a portion of a stylet, actuate jaws, actuate blades, or a combination thereof. The follower surface may be a proximal end of a guide jaw support rod, a blade support rod, a tube, a portion of a stylet, actuate jaws, actuate blades, or a combination thereof. The follower surface may include a track. The follower surface may include a groove. The follower surface may have a piece projecting therefrom that contacts a portion of the third link so that the third link is guided in a longitudinal direction of the stylet. The follower surface may be located proximal of a tube of the stylet so that upon movement of the third link the tube is moved along the stylet. The follower surface may be an external wall of one or more tubes of the stylet, one or more jaw support rods, one or more blade support rods, or a combination thereof. The third link may contact a follower surface on a first side, a second side, or both sides. The follower surface may have a stop at a first end, a second end, or both so that a travel distance of the third link is limited. The stops may prevent the third link from being removed from the follower surface. The arcuate motion of the third link may limit the longitudinal movement along the follower surface. For example, in the release position the third link may be in contact with the follower surface and as the third link moves towards the retract position (e.g., distally) a gap may form between a connection of the third link and the follower surface until the portion of the third link contacts the follower surface again and the longitudinal movement is prevented. The portion extending from the third link that contacts the follower surface may be a cam surface.

The one or more cam surfaces may function to contact a tube, the stylet, a jaw support rod, a blade support rod, or a combination thereof. The one or more cam surfaces may extend from the third link. The one or more cam surfaces may connect to a tube, the stylet, a jaw support rod, a blade support rod, or a combination thereof. The one or more cam surfaces may rotate as the third link travels longitudinally along the follower surface. The cam surface my move and the follower surface may be static. The cam surface and the follower surface may move together. The cam surface may be located entirely on one side of the third pivot or the fourth pivot. The cam surface may be located on the third link between the third pivot and the fourth pivot.

The fourth pivot may function to ground the fourth link. The fourth pivot may connect to two joint elements (e.g., a joint element in a third link and a joint element in a fourth link). The fourth pivot may provide rotational movement of the third link relative to the fourth link. The fourth pivot may prevent longitudinal movement, lateral movement, or both of the third link relative to the fourth link. The fourth pivot may allow the 4-bar mechanism to move within a housing so that the four bar mechanism moves the jaws, blade, or both between a first position (e.g., open or released) and a second position (e.g., closed or cutting). The fourth pivot may be located above, over, or both the first link, the second link, the third link, the first pivot, the second pivot, the third pivot, an axis of movement of the stylet, or a combination thereof. The fourth pivot may extend into the fourth link or be part of the fourth link.

The fourth link may function to ground one or more of the links. The fourth link may act as a stationary part for one or more of the links to rotate about, move relative to, ground the other links, or a combination thereof. The fourth link may be part of the housing. The fourth link may be connected to the first link and the third link. The fourth link may complete the four mechanism. The fourth link may be the largest link. The fourth link may be a rocker link, a coupler link, or a ground link. Preferably, the fourth link is a ground link. The fourth link may be made of plastic. The fourth link may be immovable. The fourth link may house one or more of the other links. Preferably, the fourth link houses all or a portion of the third link, the second link, or both. The fourth link may house a portion of the first link and the first link may extend out of the fourth link. The fourth link may the housing, a body, a gripping portion, a hand piece, or a combination thereof of the electrosurgical device. Preferably, the fourth link is a fixed link. The fourth link may ground one end of a return mechanism so that the first link is returned from a second position to a first position when an application of force or torque is complete.

The return mechanism may assist in actuating one or more links. The return mechanism may return the one or more links to a neutral position and/or a starting position after actuation. The return mechanism may be any device that biases one or more of the links to a resting position so that when the first link is actuated and released from actuation the tubular member, stylet, jaws, blade, or a combination thereof return back to a resting position. The return mechanism may be located on a distal side or a proximal side of one or more of the links. The return mechanism may be located on a distal side or a proximal side of a third link. Preferably, a return mechanism is located on a distal side of a third link. The return mechanism may extend around a pivot. The return mechanism may extend from a first side of a pivot to a second side of a pivot. The return mechanism may extend between a handle and trigger. The return mechanism may pull on a portion of a trigger or a link. The return mechanism may be and/or include a biasing member (e.g., a spring structure, an elastic member, a compressible member, a stretchable member, any structure that can be compressed and released, or a combination thereof). The return mechanism may be a return spring or a compression spring. The return mechanism may be connected to a proximal end of a stylet, a tubular member, a first link, a second link, a third link, a fourth link, or a combination thereof. The return mechanism may assist in moving a first link from a first position to a second position so that the jaws (e.g., forceps) of the electrosurgical device are opened. The forceps device may include both a return mechanism and an over force prevention mechanism.

The over force prevention mechanism (OFPM) may function to prevent the jaws, a blade, a link, a trigger, a handle, or a combination thereof being damages upon contact with a solid piece, a solid feature, or both. The OFPM may completely depress and prevent further actuation of the trigger. The OFPM may slide when the trigger or a link continues to have a force or torque applied (i.e., may slide to prevent failure of other parts). The OFPM may assist in creating movement in a forceps device.

The present teachings provide a forceps device. The forceps may function to grip an object. Preferably, the forceps may be used during surgery to grip a feature of interest including: a part of a body, an anatomical feature, tissue, veins, arteries, or a combination thereof. The forceps may move between a first position (e.g., release position) and a second position (e.g., retract position). The forceps may function to be used in surgery, for example laparoscopic surgery. The forceps may be used with or without power. Current may be passed through the forceps so that the forceps are used for electro-surgery. For example, a therapy current may be passed from one jaw to a second jaw when tissue is located within the jaw and the therapy current may coagulate blood, cauterize, cut, or a combination thereof. In another example, a therapy current may be passed from one or more of the jaws to a remote electrode (e.g., a return pad). The forceps may generally include one or more working assemblies and sufficient controls to work the one or more assemblies. The forceps may be comprised of parts needed to perform the recited functions and may include generally, a stylet (e.g., a tubular member, a hollow tube, or an assembly of tubes), a hand piece, one or more operable mechanisms used to actuate the stylet, or a combination thereof. The hand piece may be an assembly of parts or housing structures capable of forming a hand piece structure with a cavity. The forceps may be actuated by one or more operable mechanisms. The forceps may create a sufficient gripping force so that one or more features of interest of a patient's body may be manipulated by the gripping assembly, secured by the gripping assembly, or a combination thereof. The forceps may be composed of parts that may extend through the tubular member. The forceps may be an assembly of parts rotatable about an axis (e.g., a rotational axis of the forceps, the longitudinal axis of the tubular member, a longitudinal axis of the forceps, or a combination thereof). The forceps may grip and release while being simultaneously rotated. The forceps may be actuated by the actuation mechanism in communication with the forceps. The forceps may be actuated by retracting the two opposing jaws into the stylet (e.g., one or more tubular members) forcing the two opposing jaws closed. The forceps may be actuated by extending the one or more tubular members away from the hand piece (e.g., distally) so that the one or more tubular members move the two opposing jaws towards one another into a retracted position, creating a gripping force, or both. The forceps may generally have two or more opposing jaws, and one or more jaw shafts or legs, or a combination of both. Preferably, the forceps may have two jaw shafts or legs that each include an arcuate section and an opposing jaw attached to each of the jaw shafts or legs.

The two or more opposing jaws may function to create a gripping force. The two or more opposing jaws may move towards each other to create a gripping force, to grip a feature of interest, or both. The two or more opposing jaws may be any device that may be used to grip items of interest in surgery, for example laparoscopic surgery. The two or more opposing jaws may function to be used to grip or clamp an item of interest for cutting or applying a bipolar energy source. The two or more opposing jaws may be any shape and size so that the jaws perform a gripping function, create a gripping force, or both. Preferably, the two or more opposing jaws may be one jaw structure with another mirror image opposing jaw structure (i.e., identical) that when forced together may create a gripping function. The two opposing jaws may be any two or more structures that may be movable relative to each other for perform a gripping function. The two opposing jaws may be any structures that may allow one jaw to be static and one jaw to be movable or any combination thereof. The two opposing jaws may be one solid piece. The two opposing jaws may be formed of two wires that are shaped to have a generally "U" shaped end. The two opposing jaws may include a gap (e.g., a blade track) to allow for a cutting instrument to be inserted while retaining functionality of the two or more opposing jaws.

The gap may be any shape and size so that a blade, functional element, a surgical instrument, or a combination thereof may be extended into the gap in the jaws, into the gap between the jaws, or both. The blade, a surgical instrument, functional element, or a combination thereof may be extended into the gap formed in (or between) the two opposing jaws while the two opposing jaws are closed, open, or in a position therebetween. The gap may be formed in the opposing jaws, the jaws may be made of a wire material that may be formed to include the gap, material may be removed to form the gap, or a combination thereof. The gap (e.g., blade track) may extend along the longitudinal axis of the tubular member, blade, or both so that the blade axially extends into the gap during use. The material the jaws are made of may be formed to include a gap.

The two opposing jaws may be made of any material so that the two opposing jaws may be used to create a gripping force. The two opposing jaws may be made of a flexible material, resilient material, rigid stainless steel, a plastically deformable material, an elastically deformable material, or a combination thereof. The two opposing jaws may be made of a material that conducts electricity. The jaws may include a protective cover.

The protective cover may function to prevent current leakage, prevent application of power to an undesired location, insulate the wires, create a contact location at a predetermined location, or a combination thereof. The protective cover may protect an outside of the jaws. The protective cover may prevent stray current. The protective cover may assist in directing current to a desired location. The protective cover may be made of an insulating material. The protective cover may be made and/or include rubber, plastic, a polymer, plastic, an insulative material, or a combination thereof. The protective cover may cover only a portion of the jaws so that the jaws may apply power.

The two opposing jaws may be used to apply electricity to a feature of interest that may be gripped by the two opposing jaws. The two opposing jaws may be a first jaw and a second jaw. The first jaw may be movable relative to the second jaw, or vice versa. The first jaw and second jaw may be longitudinally movable relative to each other. Preferably, the first jaw and second jaw longitudinally move in unison. The first jaw, the second jaw, or both may laterally move relative to each other (i.e., linearly directly towards and away from each other). The gripping portion of the two opposing jaws may have a surface texture to grip a feature of interest. For instance the surface texture may be smooth, flat, contoured, serrated, textured, include ridges, mouse teeth, or a combination thereof. Preferably, the gripping portion of the two opposing jaws may have a serrated edge to allow for more secure gripping. The two opposing jaws may have an edge with a surface that may function similar to a serrated edge to allow for secure gripping. The two opposing jaws may be moved between a release position and a retract position by retraction of one of the one or more jaw shafts, movement of the one or more tubular members towards the distal end, or both along an axis of the one or more tubular members. The two opposing jaws may include a jaw bias mechanism, be part of an operable mechanism, or both. The two opposing jaws may have laterally extending arcuate sections at the proximal end (e.g., heel of the jaw) of the jaws that protrude out from the distal end of the tubular member.

The arcuate sections may function to create a ramped surface that moves the jaws towards each other. The arcuate sections may form a raised surface that is sufficiently large such that the arcuate sections do not fit within the stylet, tubular member, or both. The arcuate sections may be formed into the jaw shaft, jaw legs, or jaw support rods of the jaw shafts. The arcuate sections may be a portion added to the jaw shaft, the legs, jaw support rods, or a combination thereof. The arcuate sections when the jaws are closed may have a largest dimension that is larger than an inner largest opening of the stylet, tubular member, or both so that the arcuate sections prevent the jaws from extending into the stylet, tubular member, or both. Preferably, at least a portion of the laterally extending arcuate sections are wider than the mouth of the tubular member so that axial movement of the tubular member, the jaw shafts, or both moves the two opposing jaws closing the two opposing jaws, creating a gripping force, or both. For example, when an operable member is actuated, the one or more tubular members may be moved towards (i.e., in a distal direction or away from the hand piece) the two opposing jaws and may bias the two opposing jaws towards each other. The one or more jaws may be free of one or more arcuate segments. A proximal end of the two opposing jaws of the gripping assembly may each be attached to one or more legs, one or more jaw shafts, or both.

The one or more jaw support rods may function to assist a user in aligning a feature of interest between two or more opposing jaws, assist in creating a gripping force between the two opposing jaws, provide support to one or more jaws, extend through one or more tubular members and/or tubular members, or any combination thereof. The one or more jaw support rods may be a leg, a jaw shaft, or both. The one or more jaw support rods may extend through a central portion of the tubular member and the one or more jaw support rods are movable relative (i.e., parallel, axially, or both) to the tubular members. The jaw support rods may be generally any shape that will perform the recited functions. The jaw support rods may be any light weight material that is strong enough to support the two opposing jaws and to support the gripping action of the jaws. The one or more jaw support rods may have a cross-section that is a solid cylindrical rod, a hollow cylindrical rod, a half circle shape, or a combination thereof. The jaw support rods may include one or more flat portions, may include non-arcuate portions, may be asymmetrical, or a combination thereof. The jaw support rods may be flexible, rigid, conductive, elastically deformable, or a combination thereof. Preferably, the one or more jaw support rods may form the jaw and fold back upon itself to form an opposing leg of the jaw. For example, the jaw support rods may extend out of the tubular member and curve back into the tubular member so that the portion extending out of the tubular member forms the jaws. The one or more jaw support rods may extend through and out the tubular member at the distal end of the tubular member, at the proximal end of the tubular member, or a both. The one or more jaw support rods may extend out of the distal end of the tubular member and may have a functional attachment connected to the distal end of the one or more jaw support rods. The functional attachment may be connected to one or both of two opposing jaws or an attachment with the functional equivalent of performing a gripping function. The one or more jaw support rods may be adjacent to, extend along opposing sides, surround, or a combination thereof the cutting assembly inside the tubular member. The one or more jaw support rods may terminate in a distal end region of the tubular member, an inner tube, or both. The one or more jaw support rods may include or be connected to a follower surface, one or more bias mechanisms, or both.

The bias mechanisms may function to move the jaws, blade, or both from a release position to a retract position. The bias mechanisms may function to create a closing force, a gripping force, or both. The bias mechanism may function to actuate the jaws closed without the need for any other devices or features, to retract the blade, or both. The bias mechanism may function to bias the jaws closed, bias the jaws open, or both. The bias mechanism may only close the jaws. The bias mechanism may only open the jaws. The bias mechanism may be a combination of one or more tubes (e.g., a tubular member or an outer tube), one or more arcuate sections, or preferably a combination of both. The bias mechanism may cause the jaws to rotate about an axis. A bias mechanism may be in communication with each jaw individually. The bias mechanism may be a jaw closure mechanism. The jaw bias mechanism may be connected to a first link, a second link, a third, link, a fourth link, or a combination thereof. The bias mechanism may work in conjunction with a cutting assembly.

The cutting assembly may be any assembly of parts capable of cutting. The cutting assembly may function to cut tissue, veins, arteries, an anatomical feature, a feature of interest, or a combination thereof during a surgical procedure. The cutting assembly may be any cutting assembly that may be used in surgery, for example laparoscopic surgery. The cutting assembly may be an assembly of parts that may fit inside the tubular member and/or tubular member, extend through the stylet and/or tubular member, extend between the pair of opposing jaws, extend between legs, extend between legs and jaws, extend between jaw support rods, extend between jaws, or a combination thereof. The cutting assembly may be any assembly of parts capable of rotating independent of the tubular member or in combination with the tubular member. The cutting assembly may be actuated to perform a cutting function by an actuation mechanism. The cutting assembly may be any cutting assembly that may generally be comprised of a blade, a blade shaft, or a combination thereof.

The blade may function to cut a feature of interest. The blade may be any cutting tool that may be used in surgery, for example laparoscopic surgery. The blade may be any cutting device that may be extended and retracted through the tubular member. The blade may extend along a stylet. The blade may be made of any material that may be sharpened; is strong enough to cut a feature of interest; is biocompatible; that may conduct electricity; or a combination thereof. The blade may be any shape so that the blade may fit inside the tubular member and extend into the gap formed between the two opposing jaws, between two legs connected to a jaw, or both so that a feature of interest may be cut. The blade may be substantially solid along its length. The blade may have a length so that the blade is sufficiently long to cut a feature of interest. The maximum length of the blade may be equal to the length of the jaws. The length of the blade may be substantially equal to that of the protrusions of the camming shaft. The length of the blade may be less than that of the protrusions. The blade may include one or more recesses. The blade may be sufficiently small so that the blade may be housed in the tubular member during movement, insertion, or both. The blade may be extended into, and retracted from, the gap in the two opposing jaws. The distal end of the blade may have a shaped edge. The blade may extend distal of the jaws. The blade may conduct power. The blade may conduct a therapy current. The blade may conduct bipolar energy, monopolar energy, or both. The proximal end of the blade may be attached to a blade support rod.

The blade support rod may function to support the blade and assist in moving the blade axially. The blade support rod may extend the blade axially along the axis of the tubular member, the tubular member, or both and out of the tubular member, tubular member, or both (e.g., into the gap formed by the two opposing jaws). The blade support rod may move the blade axially upon movement of the operable mechanism, the four bar mechanism, the first link, or a combination thereof. The blade support rod may function to extend and/or retract the blade via an operable mechanism. The blade support rod may be used to actuate a blade during surgery. The blade support rod may be of shape and size to actuate a blade inside a tubular member. For example the blade support rod may be a wire, shaped metal, a rod, a plurality of combined longitudinal pieces, or any similar rigid structure that may fit in and extend through the tubular member. The blade support rod may be made of a material that is lightweight, but strong enough to extend a blade through a feature of interest thereby cutting the feature of interest. The blade support rod has a distal end and a proximal end. A blade may be attached to a distal end, a distal end region, or both of the blade support rod. The blade support rod may have a structure (e.g., a follower surface) at the proximal end of the blade support rod, at the proximal end region of the blade support rod, or both to assist in rotation of the blade inside of the stylet, tubular member, or both.

The stylet as discussed herein may include a tubular member or may be the tubular member. The stylet may have a hollow cross-section, a solid cross-section, or both. For example, an inner tube may be solid and an outer tube may be hollow. The stylet may include a tubular member and an inner tube. The stylet may include a tubular member that extends around all or a portion of an inner tube. The stylet may be a tubular member. The tubular member may function to extend into a patient during a surgical procedure so that a user (i.e., surgeon) can perform one or more surgical procedures. The tubular member may be flexible so that the tubular member may be moved within a patient. Preferably, the tubular member may be substantially rigid so that the tubular member may be moved to a desired location. The tubular member includes a distal end and a proximal end. The distal end may be an end of the tubular member that is located farthest from the hand piece (e.g., the end of the tubular member that is inserted into a patient). The proximal end of the tubular member may be the end of the tubular member located proximate to the user, in the hand piece, or both. For example, the proximal end may extend into the hand piece so that manipulation of the one or more operable mechanisms manipulates the tubular member. The tubular member may include one or more follower surfaces. The one or more follower surfaces may be manipulated by one or more cam surfaces. The tubular member and its components may be made of any biocompatible material, for example, stainless steel, plastic, a synthetic material, a natural material, or a combination thereof. The tubular member may comprise a tubular member sub-assembly. The tubular member sub-assembly may include one or more tubes, one or more inner tubes, one or more outer tubes, one or more gripping assemblies, one or more cutting assemblies, one or more rotation mechanisms, one or more operable mechanisms, one or more camming shafts, one or more guides, one or more spacing members, or a combination thereof.

The one or more outer tubes may function to close the jaws, bias the jaws, or both. The one or more outer tubes may function to house one or more jaws, one or more blades, or both. The one or more tubes may function to bias the actuation mechanisms that bias the jaws. The one or more tubes may function to protect the inner tube. The one or more jaws may move relative to the inner tube. The one or more jaws may axially move towards the distal end and the proximal end during movement. Preferably, the one or more outer tubes may be hollow. The one or more jaws may overrun the inner tube, the jaws, the arcuate sections, or a combination thereof to bias the jaws towards each other.

The one or more inner tubes may function to create a point of contact for one or more jaws. The one or more inner tubes may function to connect to a camming shaft. The one or more inner tubes may function to extend through all or a portion of the tubular member. The one or more inner tubes may form a connection point, include a connection feature (e.g., a pin, bolt, screw, rivet, or a combination thereof) for one or more jaws. The one or more inner tubes may connect to a pivot joint of one or more jaws so that the one or more jaws rotate about an axis. The one or more inner tubes may assist in opening and closing the jaws. The one or more inner tubes may be located distal of one or more tubes. The one or more inner tubes may be part of a tubular member. The one or more inner tubes may be movable relative to an outer tube. The one or more inner tubes may be axially movable, rotationally movable, or both relative to an outer tube, a camming shaft, or both. The one or more inner tubes may be static and an outer tube may be movable relative to the inner tube. The one or more inner tubes may be substantially the same length as an outer tube. The one or more inner tubes may be shorter than an outer tube. The one or more inner tubes may be in communication with a camming shaft. The one or more inner tubes may be hollow. The one or more inner tubes may be solid. The one or more inner tubes may receive all or a portion of a tube. The one or more inner tubes may be located between a tubular member and a tube.

The one or more tubular members may include and/or be one or more tubes and the one or more tubes (e.g., an inner tube, an outer tube, an intermediate tube between an inner tube and an outer tube) may function to house one or more working components (e.g., a gripping assembly, a cutting assembly, or both). The one or more tubular members may function to house all or a portion of one or more functional members (e.g., inner tube, blade, jaws). The one or more tubular members may be any device that may be used to extend a forceps device and any assemblies into a patient. The one or more tubular members may assist in actuating a gripping assembly. The one or more tubular members may include a follower surface. The one or more tubular members may be a cannula. The one or more tubular members may be flexible. The one or more tubular members may include a curve, a bend, or a combination thereof. Preferably the one or more tubular members may be rigid. More preferably, the one or more tubular members are generally linear and are substantially rigid. The one or more tubular members may be any tube shaped structure that may rotate around a longitudinal axis, its own longitudinal axis, or both. The one or more tubular members may include a distal end and a proximal end. The one or more tubular members may include an inner circumscribed diameter and an outer circumscribed diameter. The one or more tubular members may include a main body with a consistent inner and outer circumscribed diameter and a tapered portion with a larger outer circumscribed diameter than the main body. The one or more tubular members, the camming shaft, or both may include one or more segments that are square, rounded, oval, irregular, or any shape that allows for the circumscribed diameter of the one or more tubular members to increase and that may allow for rotation around a longitudinal axis, or a combination thereof. The one or more tubular members may include an inner cross-sectional dimension that assists in the functioning of the one or more assemblies. The one or more tubular members may extend into a housing, from a proximal end to a distal end, or both.

The one or more housings may function to form a hand piece, enclose a portion of an operable mechanism, form a portion of a four bar mechanism, enclose a portion of a stylet, enclose one or more tubular members, or a combination thereof. The one or more housings may be a left half and a right half. The housing may be multiple pieces that are connected together. The housing may be made of plastic. The housing may be a combination of plastic and metal. The housing may include a grip. The housing may include one or more links (e.g., a cut lever/cut trigger or a clamp lever/clamp trigger) extending therefrom. The housing may house all or a portion of the four bar mechanism. Preferably, the housing is a fourth link of a four bar mechanism. The housing may have a first link that extends from the housing. The housing be a proximal end (e.g., end closest to a user) and the jaws or blade may be the distal end (e.g., end farthest from a user). The jaws, blade, first link, second link, third link, fourth link, four bar mechanism, tube, or a combination thereof may be moved between a first position (release position) and a second position (retract position).

The release position may where no external forces are acting on a clamp lever, clamp trigger, cut lever, cut link, first link, or a combination thereof. The release position may be a neutral position. The release position may be where the jaws are open. The release position may be where the blade is proximally retracted. The release position may be where a link moves to when the link is released and the bias device biases the link to a resting position. Upon an application of force or torque the link may move from a release position to a retract position.

The retract position may be where a feature of interest is gripped, cut, held, or a combination thereof. The retract position may have one or more jaws closed. The retract position may have a link fully depressed (i.e., retracted). The retract position may have a blade extended from a distal end of a stylet, tube, or both. The retract position may be where one or more links are moved towards a user.

FIG. 1 illustrates an electrosurgical device 2 having a hand piece 10 connected to a forceps device 18. The forceps device includes a stylet 4 having a tube 5 with forceps 3 including jaws 6 connected to jaw support rods 8 extending through the tube 5. The hand piece 10 includes a housing 16 with internal parts for moving the jaws 6 and a blade (not shown). A clamp trigger 12 and a cut trigger 14 extend from the housing 16 and upon movement of the clamp trigger 12 a tube 5 extends along the jaw support rods 8 biasing the jaws 6, and upon movement of the cut trigger 14 the blade (not shown) is biased. The electrosurgical device 2 has a proximal end 60 and a distal end 62.

Figure 2:
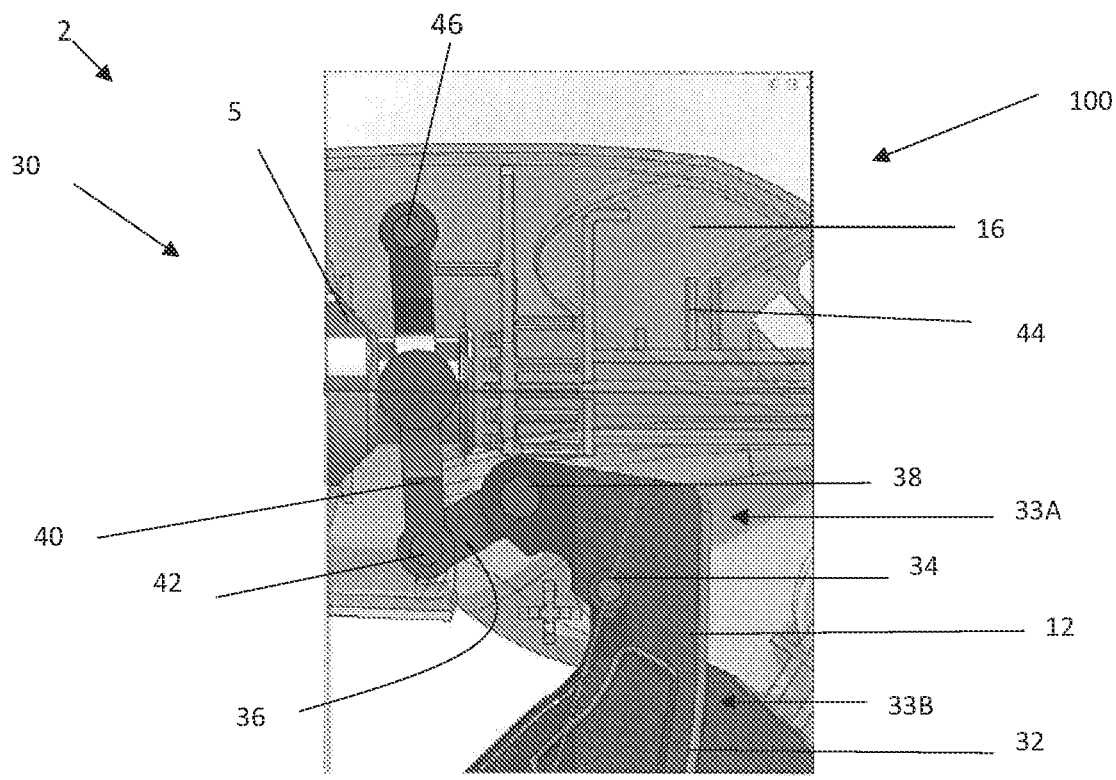
FIG. 2 illustrates a partial cross-sectional view of the laparoscopic forceps including the four bar mechanism in a release position.

FIG. 2 is an internal view of the electrosurgical device 2 and an inside of the housing 16 showing an operable mechanism (e.g., four bar mechanism) 30. The operable mechanism 30 includes a first link 32 (which is also the clamp trigger 12) that is connected to the housing 16 by a first pivot 34. The first link 32 includes a connection leg 33A and an application leg 33B. The first link 32 is also connected to a second link 36 by a second pivot 38. The second link 36 is connected to a third link 40 by a third pivot 42. The third link 40 is connected to a fourth link 44 by a fourth pivot 46. The fourth link 44 is also the housing 16 grounds the operable mechanism 30 so that the operable mechanism 30 moves the tube 5. The electrosurgical device 2 is shown in the release position 100 (i.e., first position or start position) where the operable mechanism 30 is not advancing the tube 5.

Figure 3:
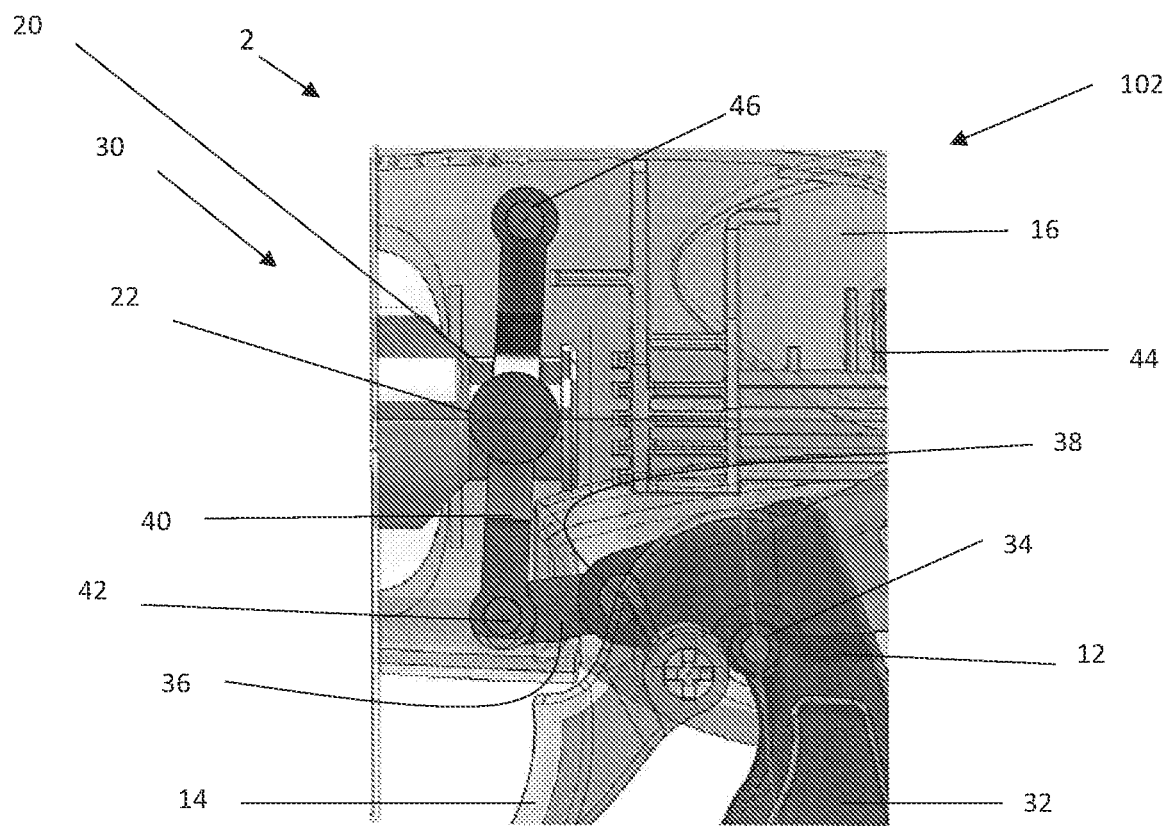
FIG. 3 illustrates a partial cross-sectional view of the laparoscopic forceps including the four bar mechanism in a retract position.

FIG. 3 illustrates the electrosurgical device 2 in the retract position 102 (i.e., second position or partial pull position) where the operable mechanism 30 is advancing the tube 5 so that tube 5 compresses the jaws (not shown) to create a gripping force. Upon retraction of the clamp trigger 12 (first link 32) the clamp lever pivots about the first pivot 34 so that the second pivot 34 is moved distally about the second pivot 38. As the second link 36 moves forward a bottom half of the third link 40 moves distally and a cam surface 22 of the third link 40 moves along a follower surface 20 to actuate the jaws (not shown). The third link 40 is connected to a fourth link 44 via a fourth pivot 46, and the fourth link 44 is the housing 16 and forms a fixed link.

Figure 4A:
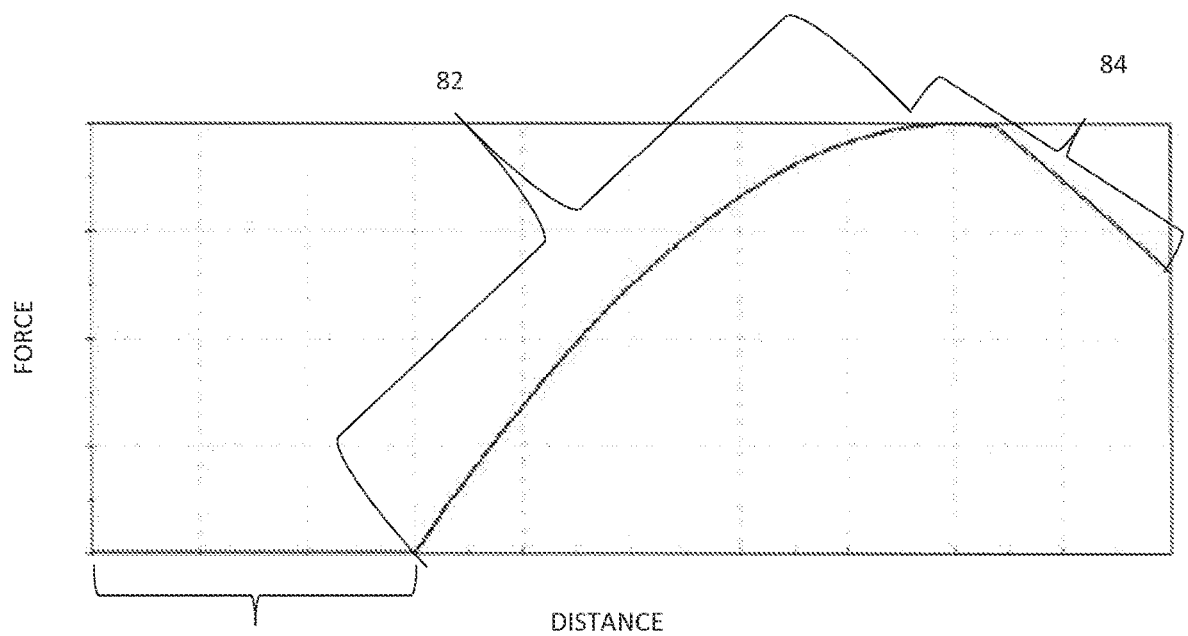
FIG. 4A is a graph depicting a change in torque as the four bar mechanism moves.

FIG. 4A is a graph depicting the changes in torque as the operable mechanism (e.g., four bar mechanism) is moved. In phase one 80 the operable mechanism freely moves a component (e.g., jaws or a blade) and the torque required by the user stays constant. Once the component creates contact (e.g., contacts another jaw or contacts tissue) the amount of torque requires increases as is shown in phase two 82. Once the component has traveled a distance an amount of force required will gradually decrease (i.e., the line has a negative slope) in a third phase 84 until full movement is achieved.

Figure 4B:
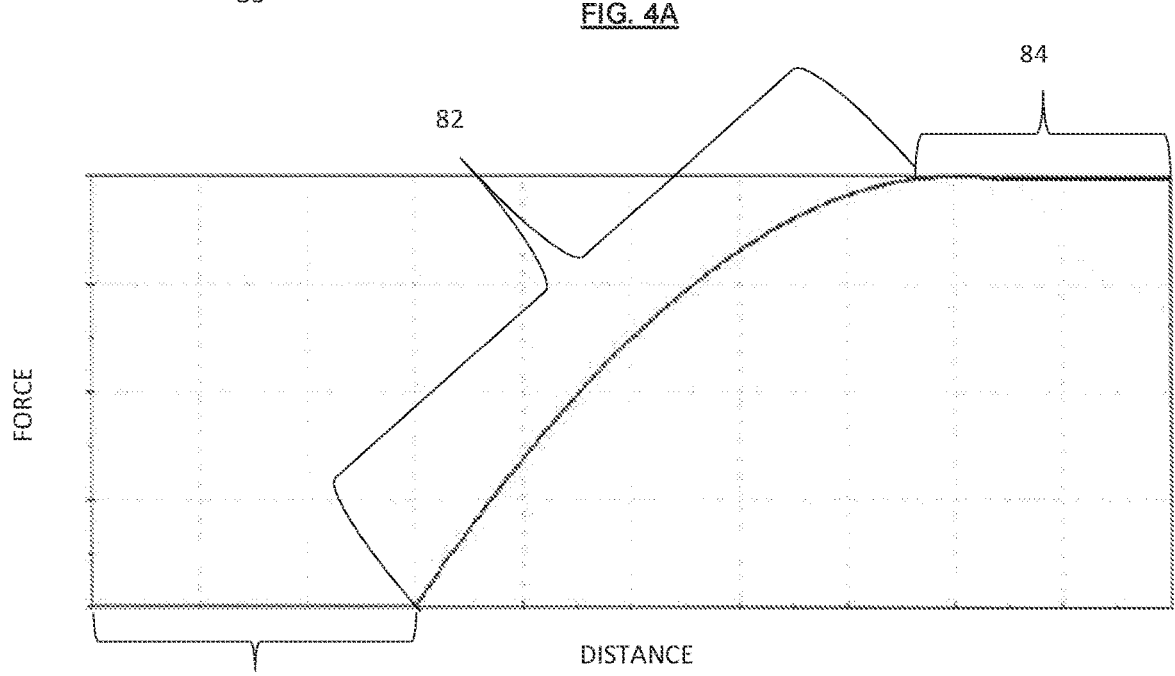
FIG. 4B is a graph depicting a change in torque as the four bar mechanism moves.

FIG. 4B is a graph depicting the changes in torque as the operable mechanism (e.g., four bar mechanism) is moved. In phase one 80 the operable mechanism freely moves a component (e.g., jaws or a blade) and the torque required by the user stays constant. Once the component creates contact (e.g., contacts another jaw or contacts tissue) the amount of torque requires increases as is shown in phase two 82. Once the component has traveled a distance an amount of force required will plateau and remain constant in a third phase 84 until full movement is achieved.

Figure 5:
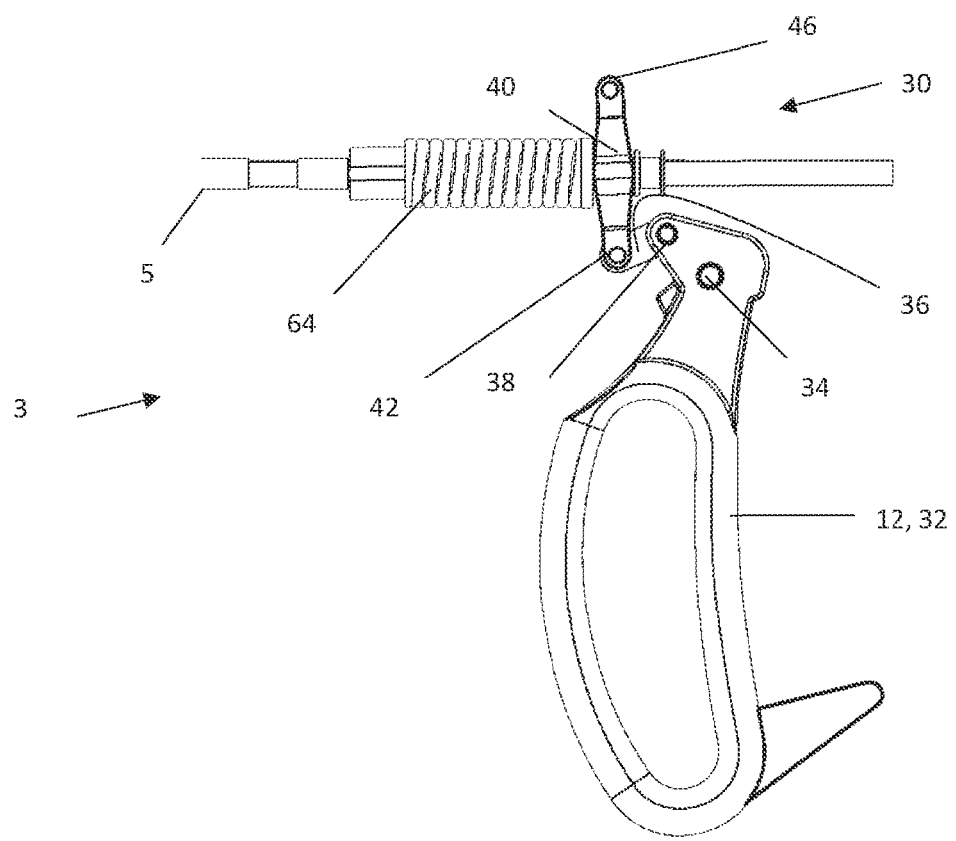
FIG. 5 is a side view of a portion of a four bar mechanism.

FIG. 5 is a side view of forceps 3 including a operable mechanism 30 connected to a tube 5, the operable mechanism 30 operating the tube 5 or a mechanism within the tube (not shown). An over-force prevention mechanism 64 is located between a third link 40 and the operable mechanism 30. The operable mechanism 30 includes a clamp trigger 12, which is a first link 32. The first link 32 is connected to a fourth link (not shown) by a first pivot 34 and second link 36 by a second pivot 38. The second link 36 is connected to a third link 40 by a third pivot 42. The third link 40 is connected to a fourth link (not shown) by a fourth pivot 46.

Figure 6:
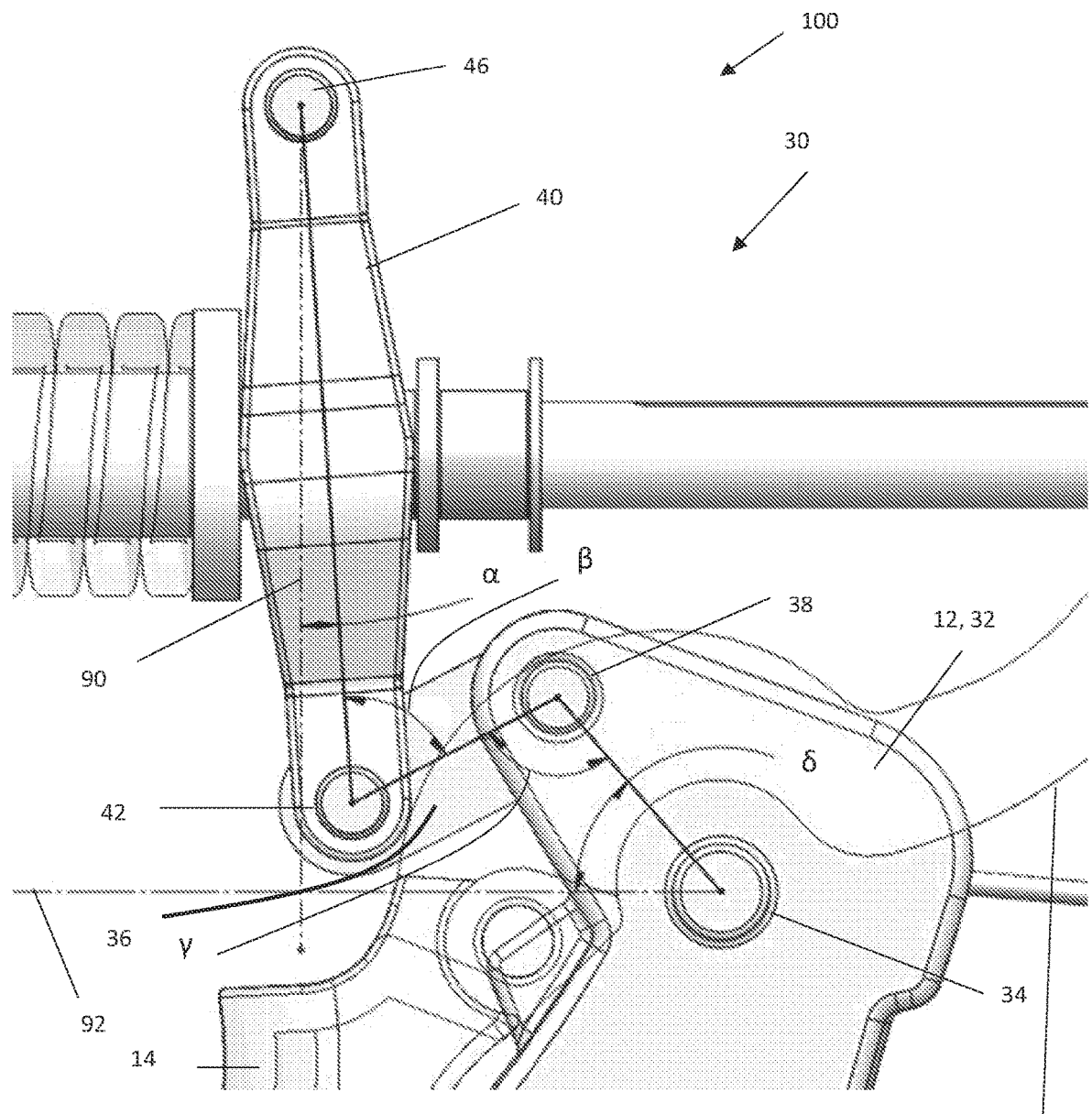
FIG. 6 is a plan view of a four bar mechanism in a release position which is a start position.

FIG. 6 is a close-up side view of an operable mechanism 30 in a release position 100 (i.e., start position). The operable mechanism 30 includes a cut trigger 14 and a clamp trigger 12, which is a first link 32. The first link 32 is connected to a fourth link (not shown) by a first pivot 34 and second link 36 by a second pivot 38. The second link 36 is connected to a third link 40 by a third pivot 42. The third link 40 is connected to a fourth link (not shown) by a fourth pivot 46. An angle (α) is located between the line extending between the fourth pivot 46 and the third pivot 42 and a vertical reference line 90. An angle (β) extends between the line extending between the fourth pivot 46 and the third pivot 42 and a line extending between the third pivot 42 and the second pivot 38. An angle (γ) extends between the line extending between the third pivot 42 and the second pivot 38 and the line extending between the second pivot 38 and the first pivot 34. An angle (δ) extends between the line extending between the second pivot 38 and the first pivot 34 and a horizontal reference line 92. As shown, the vertical reference line 90 and the horizontal reference line 92 are perpendicular to one another.

Figure 7:
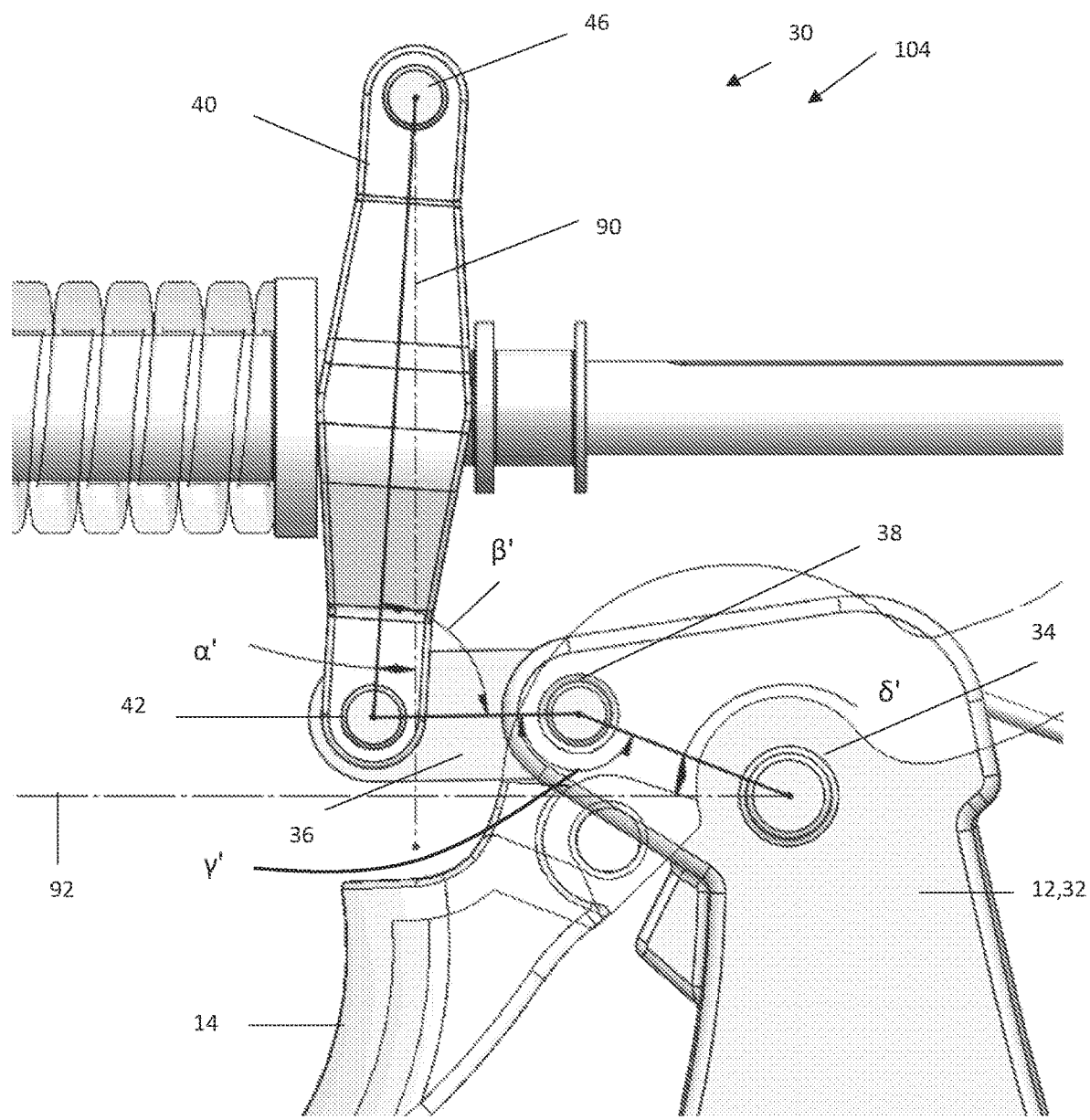
FIG. 7 is a plan view of a four bar mechanism in a partial pull position.

FIG. 7 is a close-up side view of an operable mechanism 30 moved from the starting position (FIG. 6) to a partial pull position 104. The operable mechanism 30 includes a cut trigger 14 and a clamp trigger 12, which is a first link 32. The first link 32 is connected to a fourth link (not shown) by a first pivot 34 and second link 36 by a second pivot 38. The second link 36 is connected to a third link 40 by a third pivot 42. The third link 40 is connected to a fourth link (not shown) by a fourth pivot 46. An angle (α') is located between a line extending between the fourth pivot 46 and the third pivot 42 and a vertical reference line 90. An angle (β') extends between the line extending between the fourth pivot 46 and the third pivot 42 and a line extending between the third pivot 42 and the second pivot 38. An angle (γ') extends between the line extending between the third pivot 42 and the second pivot 38 and the line extending between the second pivot 38 and the first pivot 34. An angle (δ') extends between the line extending between the second pivot 38 and the first pivot 34 and a horizontal reference line 92. As shown, the vertical reference line 90 and the horizontal reference line 92 are perpendicular to one another.

Figure 8:
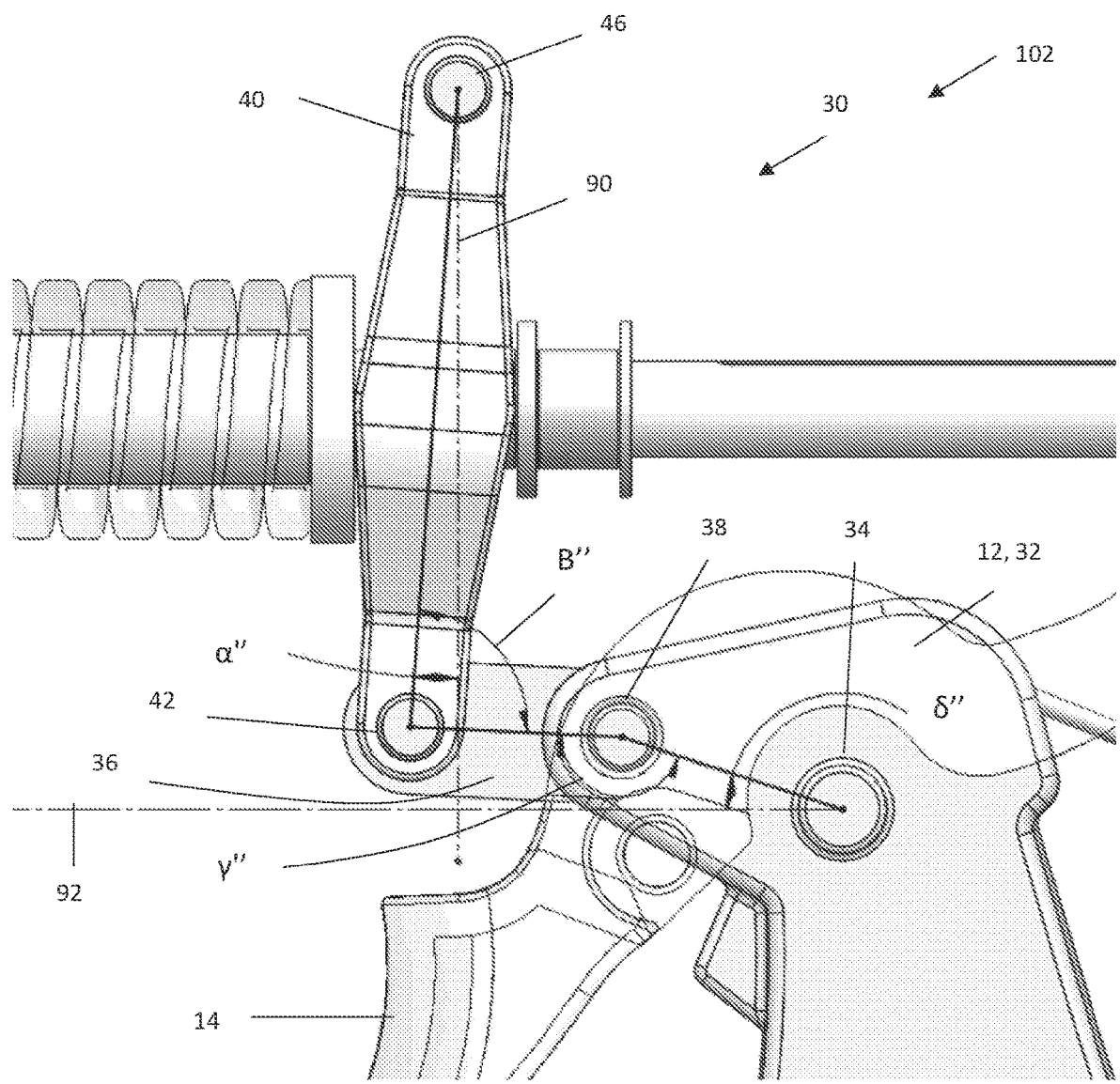
FIG. 8 is a plan view of a four bar mechanism in a retract position which is a full pull position.

FIG. 8 is a close-up side view of an operable mechanism 30 moved from the partial pull position (FIG. 7) to a retract position 102 (i.e., full pull position). The operable mechanism 30 includes a cut trigger 14 and a clamp trigger 12, which is a first link 32. The first link 32 is connected to a fourth link (not shown) by a first pivot 34 and second link 36 by a second pivot 38. The second link 36 is connected to a third link 40 by a third pivot 42. The third link 40 is connected to a fourth link (not shown) by a fourth pivot 46. An angle (α") is located between a line extending between the fourth pivot 46 and the third pivot 42 and a vertical reference line 90. An angle (β") extends between the line extending between the fourth pivot 46 and the third pivot 42 and a line extending between the third pivot 42 and the second pivot 38. An angle (γ") extends between the line extending between the third pivot 42 and the second pivot 38 and the line extending between the second pivot 38 and the first pivot 34. An angle (δ") extends between the line extending between the second pivot 38 and the first pivot 34 and a horizontal reference line 92. As shown, the vertical reference line 90 and the horizontal reference line 92 are perpendicular to one another.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

2 Electrosurgical device
3 Forceps
4 Stylet
5 Tube
6 Jaws
8 Jaw support rods
10 Handpiece
12 Clamp trigger
14 Cut trigger
16 Housing
18 Forceps device
20 Follower surface
22 Cam Surface
30 Four Bar Mechanism (operable mechanism)
32 First Link
33A Connection leg
33B Application leg
34 First pivot
36 Second Link
38 Second pivot
40 Third Link
42 Third pivot
44 Fourth Link—Fixed Link
46 Fourth pivot
60 Proximal
62 Distal
64 Over Force Prevention Mechanism
66 Return Mechanism
80 Phase 1
82 Phase 2
84 Phase 3
90 Vertical reference line
92 Horizontal reference line
100 Release Position
102 Retract Position
104 Partial Pull Position

We claim:

1. An electrosurgical device comprising:
a. a stylet including:
i. a first jaw;
ii. a second jaw that is movable relative to the first jaw from a first position where the first jaw and the second jaw are open to a second position where the first jaw and the second jaw move towards each other to grasp tissue therebetween; and
iii. one or more jaw support rods connected to the first jaw, the second jaw, or both; and
b. a housing connected to the stylet and the stylet extending from the housing, the housing including:
i. an operable mechanism including:
1. a fourth link;
2. a second link;
3. a first link being connected to the fourth link via a first pivot and being rotatable relative to the first pivot, and connected to the second link at a second pivot so that movement of the first link moves the second link relative to the fourth link; and
4. a third link being connected to the second link at a third pivot so that movement of the second link moves the third link, and the fourth link being connected to the third link at a fourth pivot, the third link moving about the fourth pivot to move the one or more jaw supports so that the first jaw and the second jaw are moved between the first position and the second position; and
wherein the fourth link is the housing and the first link is a clamp lever that extends outside of the housing and is actuated by a user; and
wherein the second link extends at an angle relative to the first link and the angle is restricted to a range between 45 degrees and 180 degrees, and the second link extends at an angle relative to the third link and the angle is between 30 degrees and 130 degrees.

2. The electrosurgical device of claim 1, wherein the second link and the third link are located within the housing.

3. The electrosurgical device of claim 1, wherein the stylet includes one or more tubes and the one or more jaw support rods extend through the one or more tubes.

4. The electrosurgical device of claim 3, wherein the third link moves at least one of the one or more tubes relative to the one or more jaw support rods to move the first jaw and the second jaw between the first position and the second position.

5. The electrosurgical device of claim 1, wherein movement of the one or more jaw support rods imparts movement of the first jaw member and the second jaw member between the first position and the second position.

6. The electrosurgical device of claim 1, wherein the third link has one or more cam surfaces and the one or more jaw support rods include a follower surface that upon movement of the one or more jaw support rods the first link creates relative movement between the cam surface and the follower surface to translate the first jaw and the second jaw to move between the first position and the second position.

7. The electrosurgical device of claim 1, wherein the angle between the second link and the first link stays in a range within about 175 degrees and about 60 degrees throughout a full range of motion.

8. The electrosurgical device of claim 1, wherein the angle between the second link and the third link stays in a range between about 90 degrees to about 45 degrees.

9. The electrosurgical device of claim 1, wherein the fourth pivot is located above an axis of movement of the stylet.

10. The electrosurgical device of claim 9, wherein movement of the first link proximally pushes the second link at the second pivot, the second link pushes the third link at the third pivot, and the third link pushes the jaw support rod so that the first jaw and the second jaw move from the first position towards the second position.

11. The electrosurgical device of claim 1, wherein movement of the first link proximally moves the one or more jaw support rods or a blade towards a partial pull position or a full pull position.

12. The electrosurgical device of claim 1, wherein the operably mechanism includes a fifth link and the one or more jaw support rods are the fifth link that provide an output to the first jaw, the second jaw, or both.

13. The electrosurgical device of claim 1, wherein the first link, the third link, or both are rocker links.

14. The electrosurgical device of claim 1, wherein the second link is a coupler.

15. The electrosurgical device of claim 1, wherein the fourth link is a ground.

16. The electrosurgical device of claim 1, wherein movement of the first link proximally pushes the second link at the second pivot, the second link pushes the third link at the third pivot, and the third link pushes the jaw support rod so that the first jaw and the second jaw move from the first position towards the second position.

17. The electrosurgical device of claim 1, wherein movement of the first link proximally pulls the second link at the second pivot, the second link pulls the third link at the third pivot, and the third link moves the jaws from the first position towards the second position.

18. The electrosurgical device of claim 1, wherein the first link, the third link, or both are rocker links; the second link is a coupler; the fourth link is a ground; and movement of the first link proximally pushes the second link at the second pivot, the second link pushes the third link at the third pivot, and the third link pushes the jaw support rod so that the first jaw and the second jaw move from the first position towards the second position.

19. An electrosurgical device comprising:
a. a stylet including:
i. a first jaw;
ii. a second jaw that is movable relative to the first jaw from a first position where the first jaw and the second jaw are open to a second position where the first jaw and the second jaw move towards each other to grasp tissue therebetween; and
iii. one or more jaw support rods connected to the first jaw, the second jaw, or both; and
b. a housing connected to the stylet and the stylet extending from the housing, the housing including:
i. an operable mechanism including:
1. a fourth link;
2. a second link;
3. a first link being connected to the fourth link via a first pivot and being rotatable relative to the first pivot, and connected to the second link at a second pivot so that movement of the first link moves the second link relative to the fourth link; and
4. a third link being connected to the second link at a third pivot so that movement of the second link moves the third link, and the fourth link being connected to the third link at a fourth pivot, the third link moving about the fourth pivot to move the one or more jaw supports so that the first jaw and the second jaw are moved between the first position and the second position; and
wherein the fourth link is the housing and the first link is a clamp lever that extends outside of the housing and is actuated by a user; and
wherein the first link, the third link, or both are rocker links; the second link is a coupler; the fourth link is a ground; and movement of the first link proximally pulls the second link at the second pivot, causing the second link to simultaneously pull the third link at the third pivot, and causing the third link to simultaneously move the jaws from the first position towards the second position.

* * * * *